United States Patent [19]

Sibi et al.

[11] 4,003,156
[45] Jan. 18, 1977

[54] PROCESS FOR OBTAINING VARIANTS OF PLANTS WITH IMPROVED CHARACTERISTICS

[75] Inventors: Monique Sibi, Orsay; Yves Demarly, Versailles, both of France

[73] Assignee: Agence Nationale de Valorisation de la Recherche (ANVAR), Neuilly-sur-Seine, France

[22] Filed: June 17, 1975

[21] Appl. No.: 587,611

[30] Foreign Application Priority Data

June 20, 1974 France .............................. 74.21535

[52] U.S. Cl. .................................. 47/58; 47/DIG. 1
[51] Int. Cl.² ...................... A01G 1/00; A01H 1/00
[58] Field of Search .......................... 47/58, DIG. 1

[56] References Cited

UNITED STATES PATENTS

| | | | |
|---|---|---|---|
| 3,514,900 | 6/1970 | McDade | 47/58 |
| 3,683,550 | 8/1972 | Corlett et al. | 47/58 |
| 3,816,960 | 6/1974 | Gudin et al. | 47/58 |
| 3,832,801 | 9/1974 | Carlson et al. | 47/58 |
| 3,846,937 | 11/1974 | Staba et al. | 47/58 |

OTHER PUBLICATIONS

Variations within—, Sievert et al, Amer. Journ. Botany 52(7), 1965, pp. 742–750 cited.
Callus, Plantlet Formation—, Niizeki et al., Can. Journ. Botany, 49, 1971, pp. 2041–2051 cited.

*Primary Examiner*—Robert E. Bagwill
*Attorney, Agent, or Firm*—Oblon, Fisher, Spivak, McClelland & Maier

[57] ABSTRACT

The present invention relates to a process for obtaining plants having improved characteristics. This process consists in placing and culturing on a specific synthetic, non-morphogenic nutrient medium the tissues obtained from the germination of the seeds of a single seed-plant, in sub-culturing the calluses so formed on a morphogenic medium and on potting up the plants so obtained.

27 Claims, 4 Drawing Figures

FIRST STEP: Non-morphogenic culture

SECOND STEP: Morphogenic culture

THIRD STEP: Potting up

FOURTH STEP: Crossing

FIG.1

FIRST STEP: Non-morphogenic culture callus

SECOND STEP: Morphogenic culture

THIRD STEP: Potting up

FOURTH STEP: Crossing hybridization

FIG.2 (TABLE III)

COLOR OF CALLUSES:

- BRIGHT GREEN
- CLEAR GREEN
- OPALESCENT GREEN
- YELLOW
- BEIGE
- OCHRE
- NECROSED

TYPE OF DIFFERENTIATION:

NODULES, ROOTS OR ABSORBENT HAIRS

ABNORMAL OR "FOLIOLATED" LEAVES

NEOFORMED PLANTS WITH BROAD OR FILIFORM LEAVES

OBSERVATION AT SIX WEEKS

PRIMARY CALLUSES - AVERYA E 27

FIG. 3 (TABLE IV)

FIRST SUB-CULTURING

OBSERVATION AT ONE WEEK

| GROWTH SUBSTANCES g/l. / BASIS MEDIUM | I | II | III |
|---|---|---|---|
| A, $10^{-4}$ | | | |
| A, $5 \cdot 10^{-4}$ | | | |
| K, $10^{-4}$ | | | |
| K, $5 \cdot 10^{-4}$ | | | NECROSED |
| AK, $10^{-4}$ | | | |
| AK, $5 \cdot 10^{-4}$ | | | |

FIG. 4 (TABLE V)

OBSERVATION AT SIX WEEKS

| GROWTH SUBSTANCES g/l. / BASIS MEDIUM | I | II | III |
|---|---|---|---|
| A, $10^{-4}$ | | | |
| A, $5 \cdot 10^{-4}$ | | | |
| K, $10^{-4}$ | NECROSED | START OF NECROSE | NECROSED |
| K, $5 \cdot 10^{-4}$ | SUB-CULTURING No. 2 | | NECROSED |
| AK, $10^{-4}$ | | | |
| AK, $5 \cdot 10^{-4}$ | | | |

PROCESS FOR OBTAINING VARIANTS OF PLANTS WITH IMPROVED CHARACTERISTICS

The present invention relates to the improvement of plants by the creation of entirely new phenotypic characters, preserved in the case of plant propagation and immediately fixed in the case of genetic multiplication, without loss of the benefits obtained by previous characteristic genetic selections.

In a plant, the cellular function may be considered as being determined by a "crude" genetic potential identical in each of the subject's nucleus and by the epigenetic system or environment which modulates said fixed function in its regulation. In the present disclosure, the expression "epigenetic system or environment" designates a set of variables occurring in cellular function, namely:

1. the cytoplasmic gel containing the metabolizing elements, and constantly subjected to particular biochemical and biophysical equilibria,
2. the membranous and intracytoplasmic structures such as chloroplasts and mitochondria,
3. the effects onto which are superimposed those of the position of each of the cells, with respect to the entire plant, resulting in functioning oriented in a particular direction and with respect to other cells resulting in a coordinated function thereof,
4. the fluctuating environmental medium in which the plant grows.

When subjected to all these factors, the expression of which is repeated in an identical manner in each generation, the genetic information can be expressed in various ways, as is shown by the heterophyllous character of some plants, such as, for example, *Sagittaria sagittifolia*, *Salvinia*, etc.

According to the present invention, it has been found possible, starting with a single, constant genetic information, to obtain various expressions thereof simply by modifying the epigenetic environment, the modification being realized in response to pressures brought to bear on cells by in vitro tissue culture.

The variability of regenerated plants obtained by in vitro tissue culture has already been studied. In this connection, may be mentioned the work of Lutz (Rev. Gen. Bot., 1969, 76, 309–359) on the study of the morphogenetic aptitudes of tissue cultures; this article teaches that in addition to a basic medium such as the "KNOP" medium (see "Culturing plant tissues" by R. J. GAUTHERET, 1959 — Ed. Masson and Co) or the "J. MURASHIGE and F. SKOOG medium" (1962 — Revue Physiologia Plantarum, 15 p. 473) the common strain of tobacco also requires kinetin and IAA (indolacetic acid) or kinetin and 2–4 D (2,4-dichlorophenoxyacetic acid).

J. Mousseau has also studied the variability of a plant population obtained from the neoformations of tobacco buds in vitro (C.N.R.S. International Symposium 293 — plant tissue culture, Strasbourg, 234–239).

Studies have also been conducted on other plants; the work of Pelletier et al (Ann. Amelior. Plantes 1971; 21, (2) 221–233) on the in vitro culture of white clover tissues may be mentioned in this connection.

The process of the present invention, which will be described in greater detail below, makes it possible, to obtain variants of plant having unique and fixed genetic characteristics, to obtain "variants" by the modification of the epigenetic environment, the characteristics of which are maintained after several selfing or self-fertilization steps. By crossing these variants, and without introducing strange genes, a more vigorous plant is obtained. The expression "more vigorous" used in the present disclosure, characterizes a plant which grows better and more quickly and which is more resistant, notably to bad weather, to organisms such as, for example, viruses and fungi, and other factors which normally disturb plant growth, compared with a control plant of the same variety obtained by normal reproduction.

In the present disclosure, the term "plant" includes agronomic plants and vegetables. As an example of agronomic plants to which the process of the invention can be applied may be mentioned wheat, barley, soya, rape, corn, and notably homozygot progeny $F_1$ of corn hybrids and the like; as examples of vegetables which can be used according to the invention may be mentioned lettuce, peas, beans and the like.

The process of the present invention comprises the following steps of 1. placing and culturing on a synthetic nutrient medium the tissues obtained from the germination of the seeds of a single seed-plant, the nutrient culture medium essentially consisting of a basic medium formed, on the one hand, of mineral salts, vitamins, iron and saccharose and, on the other hand, growth substances in an amount sufficient to ensure the formation of calluses.
2. sub-culturing the calluses so formed on a morphogenic medium consisting of the above basic medium having different contents of saccharose and growth substances, and
3. potting up the plants so obtained.

By selfing of the plants obtained in the preceeding steps there is obtained, in a surprising and unexpected manner, progeny families having fixed genetic characteristics without the introduction of strange genes. By crossing between these families a supplementary vigour appears.

Thus, according to a preferred mode of the invention, the process for obtaining variants of plants having improved characteristics, comprises the following steps:

1. placing and culturing, on the nutrient medium described hereinabove, cotyledons or tissues obtained by germinating the seeds of a single seed-plant to form calluses,
2. sub-culturing the calluses so formed on the previously described morphogenic medium,
3. potting up the plants obtained
4. multiplying the plants by the sexed way.

According to the present invention, the seeds obtained from a single variety of plant, that is to say, a plant possessing fixed genetic characteristics or, in other words, a homozygote plant, are germinated under sterile conditions. An example of the procedure for germinating seeds under sterile conditions will be given below with respect to lettuce.

The synthetic nutrient medium used in the first step of the process of the present invention is a non-morphogenic medium consisting, as was stated above, a basic medium consisting of mineral salts, vitamins, iron and saccharose and, of suitable growth substances.

In the process of the present invention, a mixture of mineral salts consisting of macroelements and microelements is used; examples of macroelements and microelements suited to the purposes of the invention will be given further on in the present description.

Among the growth substances suited to the purposes of the present invention may, for example, be mentioned α-indol butyric acid (IBA), α-naphthalene-acetic acid (NAA) 6-furfurylamino-purine (kinetin), 2,4-dichlorophenoxy-acetic acid (2,4 D) or indolacetic acid (IAA), benzyladenine (BA) or any other similar growth substance commonly used in the art. The names or abbreviations given in brackets above are those currently used to designate the said growth substances and will be used hereinafter in the present description. Routine trials will easily reveal to the skilled man in the art the concentrations of growth substances suited to the purposes of the present invention.

According to the present invention, culture on a synthetic nutrient medium is advantageously carried out at a temperature in the range of about 18° to 23° C with day lengths of about 0 to 18 hours, under lighting conditions which are the most effective to favor chlorophyll assimilation; said conditions are easily determined by one skilled in the art.

The nutrient medium may optionally contain a gelling substance, such as agar. In the case of liquid culture media casein hydrolysate and coconut milk may be used.

The pH of the media used in the invention can vary within broad limits without disturbing callus growth. However, for reasons connected with the solidification of gelose, it is preferred to use a pH in the range of 5.7 to 6.5. In the case of liquid media, pHs in the range of 5.5 to 6.5 are suitable.

Iron is advantageously added to the nutrient medium in the presence of a chelating agent, for example, in the presence of ethylene diamine tetra acetic acid (EDTA).

According to the invention, it is particularly advantageous to maintain the callus under non-morphogenic conditions for a minimum of 2 or 3 successive sub-culturing steps.

The calluses so formed are then sub-cultured into a morphogenic medium. The morphogenic medium used according to the present invention consists of the basic medium used in the non-morphogenic culture step, a basic medium in which the saccharose level is different from the level in the non-morphogenic medium, and of one or more growth substances. A single sub-culturing step is carried out and the callus is left to regenerate.

The concentration of growth substances in the morphogenic medium differ from those in the non-morphogenic medium; routine trials will make it easy for the skilled man in the art to determine said concentrations; generally speaking, however, the morphogenic medium will not contain 2,4 D when this substance is present in the non-morphogenic medium.

The plants thus obtained will subsequently be potted up and grown first under conditions substantially identical to those used for the morphogenic culture which will be defined hereinafter in the case of lettuce, and then progressively subjected to normal atmospheric conditions (cultivation in the open air).

The process of the invention is illustrated diagrammatically in

FIG. 1 appended to the present disclosure.

The present invention will now be defined in greater detail with reference to lettuce by way of example and not in any limitative a sense.

In the present description the term "lettuce" is used in its broadest botanical sense. It is synonymous with the more exact botanical definition "*Lactuca sativa L.*" A relevant bibliographical reference to the entire species is: "Cultures maraicheres" by Laumonnier R - 1962 (J. B. Bailliere, Nelle Encyl. Agricole 2nd volume).

As was stated hereinabove, the seeds are germinated under sterile conditions; lettuce seeds are advantageously germinated using the following procedure, After having been soaked in a wetting agent such as, for example, the product known by the trade name "Teepol", the seeds are sterilized in absolute alcohol and then in 8% calcuim hypochlorite for 20 minutes. They are then rinsed three times in sterile water. After being placed in a sterile manner on moist filter paper in a Petri dish they are stored in a refrigerator at 4° C for 48 hours in order to regularize germination and to eliminate any possible dormancy.

Germination occurs in a greenhouse or stove at a temperature in the range of about 20° C to 23° C; it can be conducted in the dark, in which case the stalk grows to a considerable length, or in daylight with, for example, between 8 and 12 hours illumination, which results in quicker germination and a shorter stalk.

After four or five days, a white radicle covered with hairs appears, followed by dark green cotyledons, which are then cultured in vitro under sterile conditions according to the process of the invention.

The culture medium used in the process of the invention is formed, as was previously stated:

A. of a basic medium containing:
1. a number of mineral salts consisting of macroelements and microelements
2. vitamins
3. iron in the presence of a chelating agent such as ethylene-diamine-tetra-acetic acid (EDTA) and
4. saccharose and B. of growth substances selected from one of the previously mentioned substances and which are preferably α-naphthalene acetic acid (NAA) and/or δ-furfurylamino purine (kinetin).

The nutrient medium may optionally contain a gelling substance such as agar. Casein hydrolysate and coconut milk may be used in the case of liquid culture media.

The pH of the media used according to the invention may vary within broad limits without disturbing the growth of the callus. However, owing to the solidification of the gelose, it is preferred to use a pH in the range of 5.7 to 6.5. In the case of liquid media suitable pH values lie in the range of 5.5 to 6.5.

The macroelements in the nutrient medium used in the process of the invention may be the following compounds: potassium and ammonium nitrates, magnesium sulphate ($MgSO_4$, $7H_2O$), calcium chloride ($CaCl_2$, $2H_2O$) and monopotassium phosphate. This combination of mineral salts constitutes what the one skilled in the art generally calls "MURASHIGE & SKOOG macroelements" (Revue Physiologia Plantarum 15, p. 473).

The microelements contained in the culture medium are manganese, zinc and copper sulphates, potassium iodide, boric acid, calcium chloride and the molybdenum-sodium oxide, this combination of elements constitutes "MURASHIGE & SKOOG microelements." According to a variant of the invention, the calcium chloride and molybdenum-sodium oxide can be replaced in the combination described above by aluminium chloride ($AlCl_3, 6H_2O$) and nickel chloride ($NiCl_2, 6H_2O$); this other combination of microelements is generally referred to as "HELLER microelements" (see "The culture of plant tissues" by GAUTHERET, mentioned.

The following are the amounts of macroelements and microelements to be used to prepare one liter of culture medium according to the invention:

| SKOOG Macroelements | | SKOOG microelements | |
|---|---|---|---|
| Salt | weight in mg/l of medium | Salt | weight in mg/l of medium |
| $NH_4NO_3$ | 1650 | $MnSO_4.(4 H_2O)$ | 22,300 |
| $KNO_3$ | 1900 | $ZnSO_4.(7 H_2O)$ | 8,600 |
| $CaCl_2.(2 H_2O)$ | 440 | $H_3BO_3$ | 6,200 |
| $MgSO_4.(7 H_2O)$ | 370 | KI | 0,830 |
| $KH_2PO_4$ | 170 | $Na_2MoO_4.(2 H_2O)$ | 0,350 |
| | | $CuSO_4.(5 H_2O)$ | 0,025 |
| | | $CaCl_2.(6 H_2O)$ | 0,025 | or according to the variant described above:

| SKOOG macroelements | | HELLER microelements | |
|---|---|---|---|
| Salt | weight in mg/l of medium | Salt | weight in mg/l of medium |
| $NH_4NO_3$ | 1650 | $H_3BO_3$ | 1,000 |
| $KNO_3$ | 1900 | $ZnSO_4.(7 H_2O)$ | 1,000 |
| $CaCl_2.(2 H_2O)$ | 440 | $MnSO_4.(H_2O)$ | 0,076 |
| $MgSO_4.(7 H_2O)$ | 370 | $CuSO_4.(5 H_2O)$ | 0,030 |
| $KH_2PO_4$ | 170 | $AlCl_3.(6 H_2O)$ | 0,050 |
| | | KI | 0,010 |
| | | $NiCl_2(6 H_2O)$ | 0,030 |

As was previously stated, the culture medium also contains the vitamins mentioned below in the following proportions for one liter of culture medium:

| Meso-inositol | 100.00 mg |
|---|---|
| Calcium pantothenate | 1.00 mg |
| Nicotinic acid | 1.00 mg |
| Vitamin B6 - Pyridoxine | 1.00 mg |
| Vitamin B1 - Thiamine | 1.00 mg |
| Biotin | 0.01 mg |

This combination of vitamins is usually referred to as "MOREL vitamins" (see the above mentioned book by GAUTHERET).

The iron is advantageously added to the nutrient medium in the presence of a chelating agent, for instance, in the presence of ethylene-diamine-tetraacetic acid (EDTA). For example, 37.2 mg of $Na_2EDTA$ and 27.8 mg of $FeSO_4$ ($7H_2O$) is used for one liter of nutrient medium, corresponding to a concentration of iron of 5.6 mg/l.

Trials have shown that each growth substance present in the culture medium used in to the process of the invention should, in the case of lettuce, be present at a concentration not higher than 1 mg/l ($10^{-3}$ g/l) of the nutrient medium; concentrations higher than 1 mg/l inhibits development of the strain. It will, on the other hand, be easy for the skilled man in the art to determine the minimal amount of growth substance to be used.

According to the present invention, a concentration of 1 mg/l of each growth substance present in the culture medium is effective for initiating callus growth and 2 to 5 times less than that amount is generally sufficient to maintain the development of secondary calluses from primary calluses. It has also been demonstrated that the growth substance NAA used in suitable amounts with the basic medium according to the invention induced root formation, that the NAA-kinetin mixture encouraged the formation of buds and that the growth substance kinetin made it possible to maintain the callus under non-morphogenic conditions. It will be easy for the skilled man in the art to determine the substance to be used and its concentration as a function of the growth stage in question.

In the case of lettuce, comparative trials carried out with synthetic media differing from those used in the process of the invention in the composition of their basic medium or in the nature of the growth substances, have shown that the culture media of the present invention are specific for the development of callus by in vitro tissue culture.

Culturing lettuce on the synthetic nutrient medium is advantageously realized according to the present invention at a temperature in the range of from 18° to 23° C with day lengths of from 0 to 18 hours, under lighting conditions which are most effective to encourage chlorophyll assimilation, these last being easy to determine by the skilled man in the art. Cultures in a liquid medium are usually carried out at about 20° C and 15 hours day length.

In the case of lettuce, root formation is not simultaneous with the development of the plantlet on the callus. Rhizogenesis may occur without the addition of growth substances but the latency time is often longer than 1 month. According to the process of the invention, the calluses are subcultured on a morphogenic medium containing a growth substance inducing the formation of plantlets and, as soon as regenerations are observed on the callus the plantlets are removed when they are large enough and are placed on a morphogenic medium containing a growth substance inducing rhizogenesis, such a medium will be designated hereinafter as a rhizogen medium. Said rhizogen medium consists of the basic medium defined hereinabove with added saccharose and a growth substance which is α-naphthalene acetic acid (NAA) or α-indole butyric acid (IBA) and agar, the agar being used in an amount sufficient to maintain the plantlets in place and not hamper the appearance of roots. According to the invention, it was found that saccharose is indispensable for the survival of plantlets, and that the total absence of agar did not encourage root formation. The pH of the rhizogen medium is advantageously in the range of 5.7 to 6.5.

A rhizogen medium particularly suited to embodiment of the invention comprises the basic medium defined hereinabove to which about 20 to 35 g, and notably 30 g per liter of saccharose and growth substance have been added. The NAA substance which is rhizogenic for calluses induces the regeneration of thick, knotty roots; furthermore, it inhibits their appearance at concentrations of $10^{-4}$ g/l and higher. The substance IBA, on the other hand, is effective at rates ten times lower and gives rise less frequently to abnormal roots. IBA is therefore the growth substance particularly preferred to the rhizogenesis of plantlets according to the invention. This second step of the process of the invention is preferably realized at a temperature in the range of about 5° to 20° C and preferably at about 15° C with about 8 hours day length; the plantlets can be potted up after a period of about 7 to 21 days.

The process of the invention makes it possible to obtain "variants" of lettuce which are different from all the variants obtained by conventional mutation methods, as will be seen from the results of trials given below. The variations induced during in vitro tissue culture modify the epigenetic environment of the cell; said epigenetic variations do not induce changes in the genome, but in the sequence and intensity of the expression of the programme or even incite the derepression of redundant genes.

The phenotype of each plant grown according to the process of the present invention is the result of interactions between an intact genetic information, the cytoplasmic disturbance induced during "tissue" culture at the level of the callus from which it is obtained, and the environmental conditions under which the plant is grown.

The cytoplasmic disturbance induced during the in vitro culture of callus tissues will be all the greater as the calluses are maintained in some sub-culturing steps under non-morphogenic conditions. Under said conditions, each cell is very weakly "specialized"; its lever, or cytoplasmic state, varies very little. A very wide field of variation is therefore open to genome functioning:

first, because weak attractors will be able to act on the cell and "deviate" its regulation, that is to say, in the modulation of the expression of the entire genome, associated with the epigenetic state;

then because the "variant" cell which appears in the callus survives easily because little is asked of it in the way of performances.

To sum up, variations will be induced preferentially during the culture of amorphous calluses, and it is only from the stage of plantlet morphogenesis that the expression of these variations may be observed. Thus, the hereditary information of neoformed plants will be able to be used or "liberated" by particular programming, differing from that of control plants.

According to the present invention it is therefor particularly preferred to maintain the calluses in nonmorphogenic conditions for a minimum of 2 or 3 successive sub-culturing steps. It is not compulsory to effect a larger number of sub-culturing steps, up to 6 or more for example, to obtain variants, but, in certain cases this may be done without inconvenience. These conditions are obtained, for example, by maintaining cultures in the dark for the primary callus stage, or by using kinetin alone, without NAA, or by dissociating the cellular masses by culturing in a stirred liquid medium; the cultures are preferably maintained in the dark from the primary callus stage and for 2 to 3 sub-culturings.

The process of the present invention is applicable to all varieties of lettuce, greenhouse varieties, winter lettuce, and the like, such as, for example, the varieties "Val d'Orge", "Gallega", "Averya $E_{27}$", "Batavia".

On the synthetic nutrient medium of the invention, there is formed a primary callus which adapts to said medium while impoverishing it and liberating new substances. Sub-culturing on a new medium, identical to the initial medium, disturbs the previously established equilibria in the callus and results in its rapid necrosis. At this stage, toxicity is avoided by decreasing the level of growth substances in the medium. Trials have shown that the phenomena of caulogenesis, proliferation, or regeneration of roots induced by the nutrient medium used for the formation of primary calluses are retained when said calluses are subcultured on the same basic medium containing about 2 to 5 times less growth substances.

The primary calluses can be used to seed a liquid medium. One month after culturing, it was observed that the calluses had exfoliated and that the cellular masses had proliferated actively, constituting a thick, yellow, yellow ochre or pale green culture depending on the calluses. Cellular multiplication in a stirred liquid medium is much quicker than on a gelose medium; this is due to the fact that the growth substances reach all the cells of the callus more rapidly, whereas on a gelose medium there is a certain latency time corresponding to the diffusion of growth substances into the inner cells of the callus; in a liquid medium constitutes one variant of the invention, notably to obtain morphogenic conditions, however, owing to their natural origin, the casein hydrolysate and coconut milk used to form the liquid medium do not permit rigorously identical media to be obtained. The preferred form of the synthetic nutrient medium according to the present invention is, therefor, the gelose form.

A very wide range of variability of neoformations is obtained by in vitro according to the invention; this visualizes the field of expression of a homozygote structure. There are all the intermediate forms between the organic prelimary shapes and the plantlet, or:

green nodules forming excresences;

leaves emerging directly from the callus

● of a peculiar texture, transparent, with a "crumpled" appearance, with an ill-defined, irregular contour, without a well structured axis or vein, ● thick, dark colour, and with a rounded or very denticulated shape ● thinner, soft green and conical in shape, buds with very narrow leaves.

No rhizogenesis is observed on these various forms which are doomed to die.

in other cases various types of plantlet develop:

1. in the form of a rosette with rather broad rounded leaves 2. with rather long internodes and "bushy", malformed axillary buds 3. having fasciations which remain during the entire growth cycle 4. with leaves differing from one plant to another, and also on the same plant:

leaves with irregular edges, petiolated cone, abnormal corrugations. These organs only appear at the beginning of morphogenesis. Subsequently, the differenciation processes become regular and the plantlet has a normal appearance.

The plantlets formed are then sub-cultured on a rhizogenic medium as was described hereinabove.

At this stage a first natural selection of plantlets occurs; only those specimens which root, can be potted up and continue their growth cycle. This demonstrates the important part played by the rhizogen medium.

When the roots have formed, the establishment in soil constitutes another counter-selection barrier. Plantlets are taken from sterile tubes with a high relative humidity, the roots and very thin leaves are very fragile; they should be handled with care and are susceptible both to dessication and to rot.

To enable plants to develop under the best possible conditions, pots are placed in a "minigreenhouse" and illuminated for 18 hours per day; in one week the atmosphere is changed from a saturation level to the level of ambient relative humidity by progressively raising the greenhouse roof.

Chromosome numberings effected on "Po" plants so obtained showed that each plant had a normal number of chromosomes, i.e., 2n = 18, identical to that of the single seed plant from which they were derived. This shows that there was no chromosome loss in the initial cell.

It was, however, observed that both morphologically and in the physiologic expression, the "Po" plants obtained showed differences when compared with controls obtained by normal reproduction from lettuce seed from a single seed plant. The following differences observed may notably be mentioned:

Po plants grew more rapidly than controls grown simultaneously in greenhouse and laboratory conditions;

in each case there was no formation of a "heart" or only very minor formation, and when the temperature was too high, the plant shot up almost immediately, development of the flower scape, the size and height of the plant, which were inferior to those of specimens grown normally out of doors.

It was also observed that there were several modes of development based on the season when Po plants were grown.

As is well known, lettuce is an autogamous plant, self fertilization is therefore easy. All the inflorescences should be enclosed in a large bag closed at the base. This excludes pollinization by insects and loss of seed from the earliest ripening flower heads.

Seeds from each regenerated "Po" plant represent the "$P_1$" plant generation. Selfing of "$P_1$" specimens gives the "$P_2$" generation, etc. Each of them is genetically analyzed by cultivation in frames.

In the "$P_1$" generation, analysis showed that segregations may appear between certain families. Once the variants which do not segregate at this "$P_1$" stage have been retained, no subsequent genic segregation occurs, and the plants always have a normal number of chromosomes (2n = 18). Furthermore, for all variants, morphological differences compared with controls were observed, notably a decrease in plant weight, a larger number of developed axillary buds, linked in most cases with the growth of a large number of axillary leaves, while the number of leaves in the "heart" rarely appeared to be modified. A tendency for the creation of a type of plant where the width and sometimes the length of the broadest leaf were narrower and sometimes shorter than controls was also observed.

Apart from the various points already mentioned with respect to tissue culture, the presence of phenomena should also be noted which are related to a derivation coupled with "memory" and "contagion" compared with cell functioning.

This suggests that cellular zones situated on the same level of a neoformed bud may have a specific cytoplasmic state if the cells which have given rise to each of these categories were in a different epigenetic state.

These facts make it possible to explain the presence of various types of leaves on a same regenerated plant.

Moreover, different types of variants were observed to appear in the same strain:

from different calluses; and
from a same callus.

Thus, two cells of a given callus do not function in an identical manner, even when they are close together, and they are all the more independant the further apart they are.

During morphogenesis of "$P_1$" and "$P_2$" plants, analysis of the number of leaves at various stages demonstrated that the behaviour of each family of variants or controls was not static. There is an evolution specific to each family during the whole growth cycle, each of them constituting a system possessing its own rhythm and regulating parameters.

As selfing of variants does not result in Mendelian type segregation, the results of reciprocal crossings of variants with controls, and of variants with one another were also studied. Diallel analyses of controls $t$ and variants of lettuce obtained from in vitro culture and then selfing showed, when the progeny obtained by crossing and those obtained by selfing were compared, that there was transmission of vigour.

Thus, according to the present invention, it is possible to obtain a more vigorous homozygote plant, from a single variety of lettuce and by crossing within said same variety, only by modification of the epigenetic environment. This new plant can be obtained in about 3 months; this is a considerable advantage compared with the prior art as, up to now, to obtain a homozygote plant, a plant of a given variety had to be crossed with one of another variety followed by the development of eight or nine generations before the plant could be fixed, i.e., before a homozygote plant was obtained.

As stated hereinabove, the process of the invention is applicable to agronomic plants such as wheat, soya, corn, barley, rape, etc. and to other vegetables.

Concerning wheat, it will be given the composition of a medium suitable for the non-morphogenic culture of tissues obtained from the germination of a single wheat seed-plant; said medium consisting:

1. of a basic medium comprising:
MILLER macroelements and microelements
FUJII vitamins ($x$ 1 or $x$ 10) and (2 $10^{-6}$ kg/l) glycine
Fe EDTA $10^{-4}$M or 0.5 $10^{-4}$M
1% agar
12% saccharose
2. a growth substance which is 2,4-dichlorophenoxyacetic acid (2,4 D) (concentration 2 $10^{-6}$ kg/l).

A morphogenic medium which is also suited to the objects of the invention in the case of wheat consists of the basic medium defined hereinabove having a saccharose content of only 2% and a growth substance which is indolacetic acid (IAA) at a concentration of $10^{-6}$ kg/l.

Examples will also be given hereafter of media suited to the non-morphogenic culture of tissues obtained from the germination of corn and soya.

NON-MORPHOGENIC MEDIUM SUITABLE FOR CORN

| a) basic medium | |
|---|---|
| MILLER microelements and macroelements defined hereinafter | |
| Saccharose | 30 g/l |
| Fe-EDTA | 5 $10^{-5}$ kg/l |
| FUJII vitamins | 1 ml/l |
| b) growth substances | |
| 2,4 D | 5.$10^{-6}$ kg/l |
| IAA | 5.$10^{-7}$ kg/l |
| Kinetin | $10^{-7}$ kg/l |

According to a particularly advantageous variant, other amino acids such as serine and inositol are added to this medium.

NON-MORPHOGENIC MEDIUM SUITED TO SOYA

| a) basic medium | |
|---|---|
| GAMBORG macroelements | 100 ml/l |
| GAMBORG microelements | 1 ml/l |
| Fe - EDTA | 10 ml/l |
| MOREL vitamins | 2 ml/l |
| Saccharose | 20 g/l |
| Agar | 7 g/l |
| b) growth substance | |
| 2,4 D | $10^{-6}$ kg/l |
| BA | $2.10^{-7}$ kg/l |
| pH of the medium | 5.8 |

Morphogenic media suited to corn and soya can be obtained from the non-morphogenic media mentioned hereinabove by modifying the amounts of saccharose and growth substances.

The MILLER and GAMBORG microelements and macroelements and FUJII vitamins are well known to the one skilled in the art. Further information may be obtained from the following articles "In vitro development of callus from the pollen of Lolium and Hordeum by D. Clapham, 1971, Z - Pflanzenzuchtg, 69, 2, 142–155 for FUJII vitamins, "Cellule Induction and organ redifferentiation of Triticum Aegilops and Agropyron by another culture" by M. KIMATA and S. SAKAMOTO, 1971, Japanese Journal of Palynology, 1, 1–8 for MILLER macro- and microelements, and "Culture methods and detection of glucanases in suspension cultures of wheat and barley" by O. L. GAMBORG and D. EVELEIGH, 1968, Canad. J. Biochem., 46, 417–421.

The invention will now be illustrated in detail by the following non-limiting examples:

EXAMPLE I

This example illustrates in vitro tissue culture according to the process of the invention. Lettuce variety "Averya $E_{27}$" was used in this example. Culturing conditions were as follows: temperature 23° C and 18 hours day length. Lighting was realized with tubes known by the trade name "GROLUX", with an intensity in the range of 5000 to 3000 lux and a wavelength in the range of 4000 to 7000 A.

Seeds were germinated by the procedure previously described. After germination for 4 or 5 days the cotyledons were put into in vitro culture.

The culture medium used had the following composition for one liter of medium.

| A) Basic medium | |
|---|---|
| 1) Macroelements | |
| Salt | weight in mg/l |
| $NH_4NO_3$ | 1650 |
| $KNO_3$ | 1900 |
| $CaCl_2$, $(2 H_2O)$ | 440 |
| $MgSO_4$, $(7 H_2O)$ | 370 |
| $KH_2PO_4$ | 170 |
| 2) Microelements | |
| Salt | weight in mg/l |
| $MnSO_4$, $(4 H_2O)$ | 22.300 |
| $ZnSO_4$, $(7 H_2O)$ | 8.600 |
| $H_3BO_3$ | 6.200 |
| KI | 0.830 |
| $Na_2MoO_4$, $(2 H_2O)$ | 0.350 |
| $CuSO_4$, $(5 H_2O)$ | 0.025 |
| $CaCl_2$, $(6 H_2O)$ | 0.025 |
| 3) Vitamins | weight in mg/l |
| Meso-inositol | 100.00 |
| Calcium pantothenate | 1.00 |
| Nicotinic acid | 1.00 |
| Vitamin B6-Pyridoxine- | 1.00 |

-continued

| | |
|---|---|
| Vitamin B1-Thiamine- | 1.00 |
| Biotin | 0.01 |
| 4) Fe-EDTA | |
| $Na_2EDTA$ | 37.2 mg |
| $FeSO_4$ $(7 H_2O)$ | 27.8 mg |
| 5) Saccharose | 20 g |
| Agar | 8 g | the agar and saccharose being added after the medium is adjusted to 1 liter.

| B) Growth substance | |
|---|---|
| — NAA | 1 mg/l |
| — Kinetin | 1 mg/l |

With such a medium, cellular proliferation is obtained on cotyledon scar tissue and after about one month the calluses are sufficiently large to be sub-cultured. The calluses are pale green in colour and fairly compact. Germination of cotyledons in the dark encourages the formation of buds when the calluses are cultured under light.

EXAMPLE 2

Comparative trials with various nutrient media.

In this example, the nutrient medium of the invention was compared with various other nutrient media, operating according to the procedure described in example 1.

Like the medium of the invention, the nutrient media used consisted of a basic medium containing one or two growth substances. The compositions of the basic media are given in table I below:

TABLE I

The composition of various basic media

| medium Number components | I | II | III | IV |
|---|---|---|---|---|
| Macroelements | SKOOG | SKOOG | SKOOG 1/2 | HELLER |
| Microelements | SKOOG | HELLER | HELLER | HELLER |
| Vitamins | MOREL | MOREL | MOREL | MOREL |
| Iron | Fe-EDTA | Fe EDTA | Fe EDTA | Fe $Cl_3$ |
| Casein hydrolysate | / | / | / | / |
| Coconut milk | / | / | / | / |
| Saccharose | 20 g | 20 g | 20 g | 20 g |
| Agar | 8 g | 8 g | 8 g | 8 g |
| pH | 5.9 | 5.9 | 5.9 | 5.9 |

The HELLER macroelements mentioned in Table I consist of the following mineral salts in amounts given below.

| HELLER macroelements Salt | amount in mg/l |
|---|---|
| $NaSO_3$ | 600 |
| $MgSO_4$, $(7 H_2O)$ | 250 |
| $PO_4H_2Na$, $(H_2O)$ | 125 |
| $CaCl_2$, $(2 H_2O)$ | 75 |
| KCl | 750 |

Medium IV contained iron in the form of $FeCl_3$ (6 $H_2O$) at a concentration of 1 mg/l.

Each of the basic media I, II, III and IV was combined with a growth substance or a group of growth substances namely:

α-naphthalene acetic acid (NAA) "A"

2,4-dichloro-phenoxy-acetic acid (2,4 D) "D"
furfuryl-amino-purine (kinetin) "K"

Growth substances A, D and K were used alone at concentrations of respectively 1 mg/l and 0.5 mg/l or used coupled two by two, the concentration of each growth substance being respectively 1 mg/l or 0.5 mg/l, therefore, a total of 48 different media were studied on which the speed of callus formation was compared, each medium being represented by 12 tubes.

For each tube, the plant material consisted of a cotyledonary pair of a plantlet. The homozygote character of lettuce justifies the relatively small number of repetitions. The medium most suited to culturing was determined according to the increase in size of the implant.

3 or 4 weeks after seeding, the calluses were all practically cylindrical in shape, and between 1 and 2 millimeters in thickness. However, their distribution over the gelose surface varied considerably from one culture medium to another. In this analysis only the volume of the callus was taken into account.

The average action on the growth of calluses of all the growth substances with respect to each of the basic media used was studied, as well as that of all the basic media with respect to each combination of growth substances.

This analysis of averages was realized by the DUNCAN test cited by M. RIVES in Ann. Amel. des Plantes, 1959, 9, p. 357–376.

DUNCAN's "new range test" method was applied. The means were then regrouped by the SCHEFFE method also cited by M. RIVES in the above-mentioned reference.

Said tests consist in comparing the "observed D" difference calculated between the means taken two by two, with each "theoretical D" term:

$$D_{th} = t(n_r, k, \alpha) \cdot \frac{s_r^2}{e \cdot b}$$

$D_{th}$ = calculated theoretical value
$t(n_r, k, \alpha)$ = value read in the table "Studentized range $t_m$" at the threshold; $\alpha$, $n_r$ degrees of freedom; $k$ representing the number of means separating the two means concerned.
$s_r^2$ = residual mean square or residual variance.
$e \cdot b$ = effective of each block $x$ number of blocks = number of representatives used in the calculation of each mean.

a. Mean analysis for each of the basic media

By the use of this method, medium II was found on an average to be less efficacious, whereas the other media appeared to be substantially equivalent.

| Media | I | II | III | IV |
|---|---|---|---|---|
| Means according to DUNCAN | 10.43 | 8.73 | 10.72 | 10.57 | b. Mean analysis for the various combinations of growth substances

The results obtained by the method described above were as follows:

| Growth substance | K - D | | A - D | | A - K | |
|---|---|---|---|---|---|---|
| Concentration in g/l | $10^{-3}$ | $5 \times 10^{-4}$ | $10^{-3}$ | $5 \times 10^{-4}$ | $10^{-3}$ | $5 \times 10^{-4}$ |
| Mean according to the DUNCAN test | 6.72 | 7.79 | 8.35 | 9.43 | 9.20 | 11.58 |
| Growth substance | A | | K | | D | |
| Concentration in g/l | $10^{-3}$ | $5 \times 10^{-4}$ | $10^{-3}$ | $5 \times 10^{-4}$ | $10^{-3}$ | $5 \times 10^{-4}$ |
| Means according to the DUNCAN test | 11.52 | 11.33 | 14.70 | 11.91 | 8.45 | 10.37 |

In the above table, and in the example in the description, the concentrations given for combinations of growth substances A-D, A-K and K-D are the concentrations of each substance.

The above results show that, on an average, kinetin and NAA at the concentrations used in this experiment, as well as the combination "NAA-kinetin" at the weakest rate, are good growth inducers, whereas substance D (2,4 D) used alone or in the presence of NAA or kinetin, and the combination "NAA-kinetin" at a high rate, appear to hinder development of the strain.

For each of the four basic media, a comparative study of the mean values of development as a function of each combination of growth substances was also effected using the DUNCAN test described above; the results given in table II below show that the best growth inducer was kinetin at a concentration of $10^{-3}$ g/l or $5.10^{-4}$ g/l according to the basic medium, the most significant development being obtained on medium III.

The effect of NAA on growth was nearly as effective as kinetin when used with medium I, or at a weak dose with media III and IV.

It should be noted that a weak concentration of this NAA-kinetin combination did not result in very substantial development, but this combination encourages an invariability of response on the four basic media.

The histological aspect was also observed; after suitable treatment, sections were stained successively with hematoxylin, alcyan blue and then eosin.

Seriated sections through soft calluses with compact green spots showed that the consistancy and colour of the calluses were associated with the type of cellular organization composing it; thus, the soft beige portions consisted of a group of cells of variable volume, which were often large and disposed anarchically. The cell walls, which appeared not to be very rigid, could be stained with alcyan blue while the cell contents were destroyed.

In another case, the compact green spots were better structured. The small, regular cells had a meristematic appearance cytoplasm and were stained deep pink by eosin. Intermingled vessels, strings of cells, cells arranged in half circles about one or more vessels, groups of cells organized in regular globules having the appearance of embryoids and also, on the callus surface, more highly developed apex, root, bud or leaf formations, started to develop.

A first observation at 3 or 4 weeks showed that soft calluses formed on medium IV and on media containing 2,4 D gave rise to small, hard chlorophyllian formations which were not numerous or were even non existent.

Apart from said media and media I with added kinetin and III containing high rates of NAA, homogeneous chlorophyllian formations were observed. It was also observed that the intensity of staining varied with the culture medium; the brightest and most compact was obtained on media I and II containing the combination NAA-kinetin at a concentration of $5 \times 10^{-4}$ g/l.

Subsequently, at about 6 weeks, the media giving chlorophyllian formations were observed, that is to say, media I, II and III containing NAA, kinetin, and NAA-kinetin growth substances, respectively at concentrations of $10^{-3}$ and $5 \times 10^{-4}$ g/l.

Figure 1:
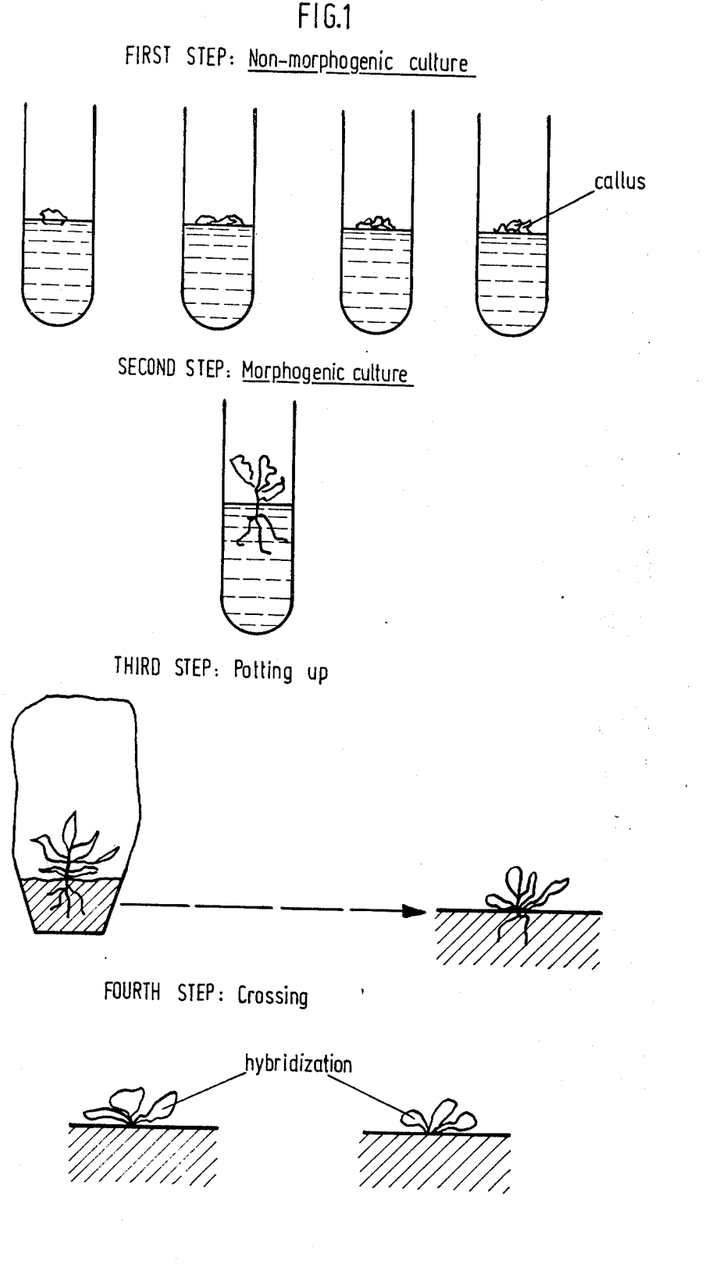
Figure 2:
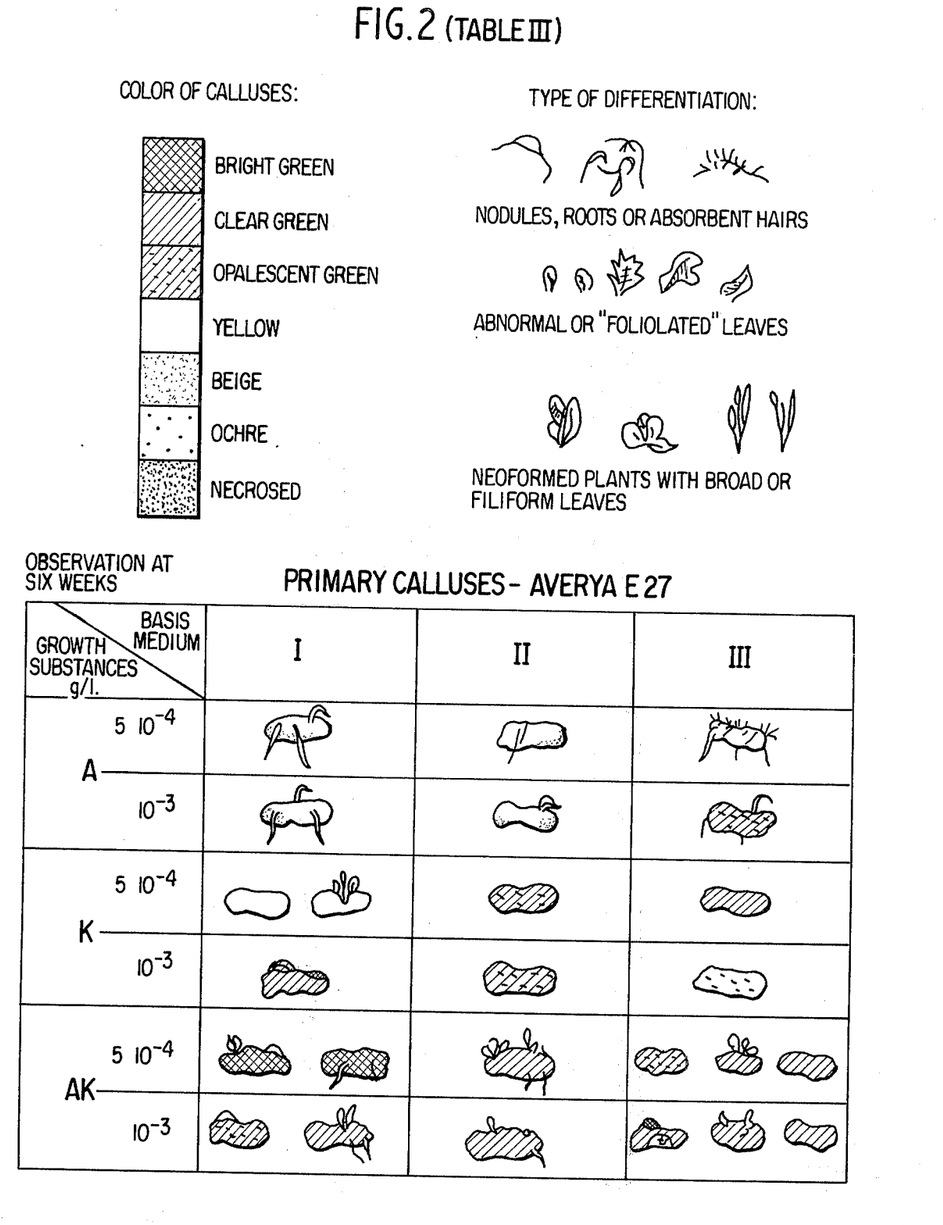
FIGS. 2, 3 and 4 illustrate the various phases of callus growth during culturing and subsequent sub-culturing.

FIG. 2 schematizes the results of notations for media giving chlorophyllian formations. Whatever the basic medium, NAA was observed to induce root formation and kinetin induced a pale green, soft proliferation which was very rarely caulogenic.

On the other hand, it was observed that the association NAA + kinetin, as a function of the basic medium and the concentration of said substances, was closely connected with the development of either normal or aberrant leaves, which sometimes grew directly from the callus, and also the formation of buds and plantlets, the calluses, however, were relatively weak.

High rates of NAA and kinetin appeared to inhibit bud development after initiation, whereas at concentrations of $5 \times 10^{-4}$ g/l the plantlets grew well and appeared to be viable.

Thus, according to the above results, kinetin is a growth substance permitting a rapid development of calluses without caulogenesis, whereas the combination NAA-kinetin induces bud formation and NAA induces root formation; on the other hand, basic media I and II are the most suitable.

EXAMPLE 3

Sub-culturing of primary calluses

Primary calluses of the variety "Averya E 27" obtained in example 2 on media I, II and III in the presence of growth substances A, K or mixtures thereof were sub-cultured respectively onto the same basic medium with the same growth substances added as in the starting media used in example 2, but the latter were used in the following concentrations:

| Growth substances | A | | K | | A-K | |
|---|---|---|---|---|---|---|
| Concentration in g/l for starting callus development | $5.10^{-4}$ | $10^{-3}$ | $5.10^{-4}$ | $10^{-3}$ | $5.10^{-4}$ | $10^{-3}$ |
| Concentration in g/l for the first sub-culture | $10^{-4}$ | $5.10^{-4}$ | $10^{-4}$ | $5.10^{-4}$ | $10^{-4}$ | $5.10^{-4}$ |

Figure 3:
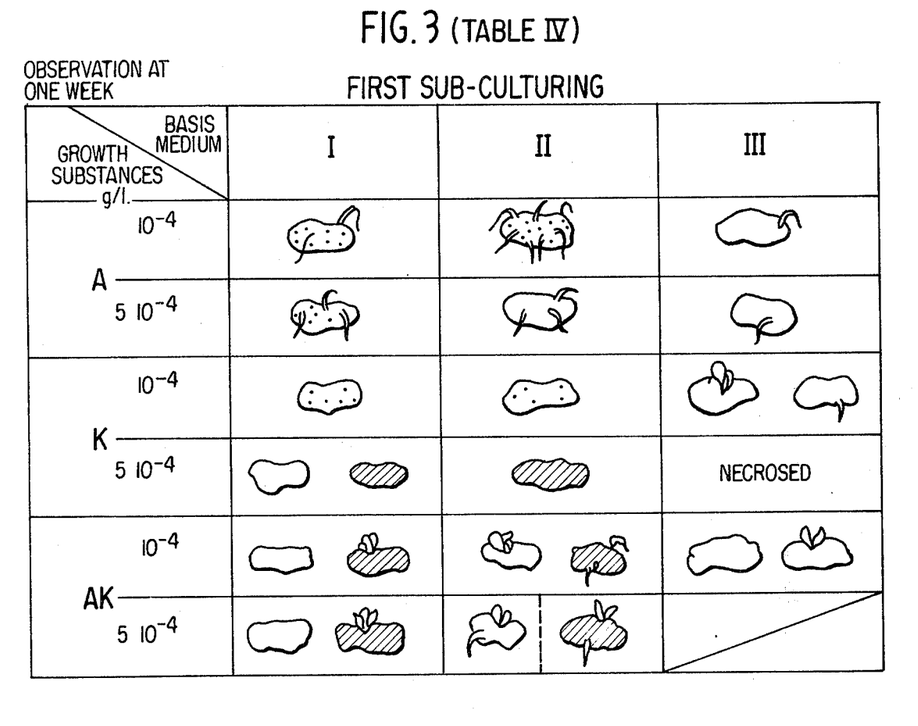
Figure 4:
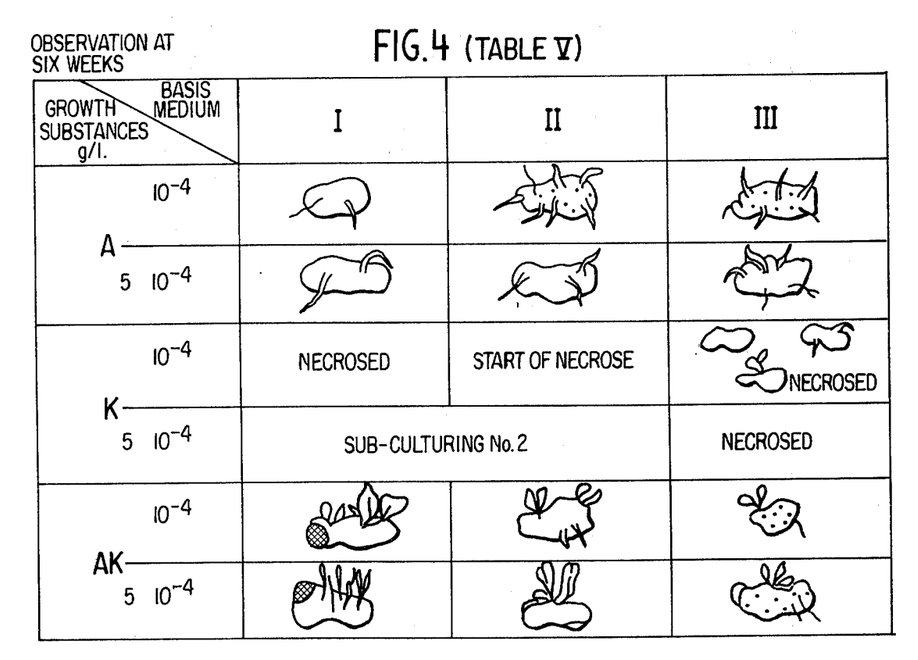

Observations at 1 week, and then at 6 weeks after sub-culturing are schematized in FIGS. 3 and 4 wherein the colour of the calluses and the types of differentiation are identical to those given in FIG. 2.

The phenomena of caulogenesis and root proliferation or regeneration induced by the preceeding medium were retained.

However, after the imbalance caused by the transfer, some strain did not succeed in readapting their functions and necrosis occurred more or less quickly.

Thus:

1: the strain on medium III containing the growth substance at a concentration of $5.10^{-4}$ g/l was necrosed in the first week after sub-culturing.

2. strain on media I and II containing growth substance K at a concentration of $10^{-4}$ g/l had several brown necrosed calluses at around the sixth week, while the other calluses developed, changing colour progressively and were stabilized, as can be seen by comparing FIGS. 2, 3 and 4.

The calluses which were mostly green often became beige, whether or not they were morphogenous, except with media I and II containing substance K at a concentration of $5.10^{-4}$ g/l. The best developed plantlets are obtained with medium I containing A-K ($10^{-4}$ g/l) and medium II containing A-K ($5.10^{-4}$ g/l) but the highest frequency of regeneration was obtained by media I and II containing mixture A-K at a concentration of $5.10^{-4}$ g/l.

In another connection, only media I and II containing substance K at a rate of $10^{-4}$ g/l is suited to the homogeneous development of non-regenerating calluses.

EXAMPLE 4

Culture in a liquid medium

The primary calluses obtained according to examples 1 or 2, from the varieties "Val d'Orge" and "Averya E

TABLE II

| | Mean analysis by the DUNCAN test | | | | | | | | | | | |
|---|---|---|---|---|---|---|---|---|---|---|---|---|
| | Growth substance concentration g/l | A | | K | | D | | A-K | | A-D | | K-D | |
| medium | | $10^{-3}$ | $5.10^{-4}$ | $10^{-3}$ | $5.10^{-4}$ | $10^{-3}$ | $5.10^{-4}$ | $10^{-3}$ | $5.10^{-4}$ | $10^{-3}$ | $5.10^{-4}$ | $10^{-3}$ | $5.10^{-4}$ |
| I | | 13.66 | 12.16 | 14.83 | 11.00 | 10.16 | 11.58 | 9.00 | 10.50 | 8.41 | 8.41 | 7.50 | 8.00 |
| II | | 9.36 | 8.70 | 12.41 | 10.50 | 6.58 | 8.33 | 8.41 | 10.25 | 7.75 | 9.66 | 7.58 | 5.25 |
| III | | 14.00 | 11.66 | 17.91 | 12.41 | 9.66 | 10.91 | 9.40 | 12.00 | 7.90 | 9.58 | 7.00 | 6.25 |
| IV | | 9.08 | 12.81 | 13.66 | 13.75 | 7.41 | 10.66 | 10.00 | 13.58 | 9.33 | 10.08 | 7.41 | 7.41 |

27", were used to seed a liquid medium. 250 ml wide mouth Erlenmeyer flasks were used containing 30 ml culture medium. The cellular groups were kept separated by agitation at a rate of 100 rotations per minute. The liquid nutrient medium used had the same composition as medium II used in examples 2 and 3 except that the agar was replaced by 20g casein hydrolysate and 100 g coconut milk.

One month after culturing calluses were observed to have exfoliated and the cellular masses were proliferating actively, constituting a thick, yellow, yellow ochre or pale green coloured culture according to the calluses.

In a stirred liquid medium, cellular multiplication was observed to be more rapid than in a gelose medium.

EXAMPLE 5

Rhizogenesis of regenerated plantlets.

In this example, the action of NAA and IBA substances on the rhizogenesis of plantlets obtained from the strain "Averya E 27" cultured on the basic medium I containing the combination A-K as growth substance at a concentration of $5.10^{-4}$ g/l was compared.

The rhizogen medium consisted, firstly, of the basic medium I previously defined (example 2) and 30 g of saccharose per liter of medium and 6 g of agar and contained, secondly, NAA or IBA at the concentrations given in FIG. 3, which gives also the results obtained after 3 weeks on one of the aforesaid rhizogen media.

Growth substance B is active at lower rates than substance A, and the formation of normal roots on all plantlets was only observed at concentrations of 20 to 30 μg.

Substance B used at the rates given above therefore makes it possible to obtain more rapid rhizogenesis on a larger number of plantlets.

EXAMPLE 6

Development in non-sterile conditions — pot culture

The plantlets potted up in this example were taken from the strains "Val d'Orge" and "Averya E 27", calluses of which were cultured according to the invention and placed under non-morphogenic conditions for about ten successive sub-culturings then induced to regenerate.

Table VI

| Number of rooted plants : number of tested plants | | | | | | | |
|---|---|---|---|---|---|---|---|
| Observation at 3 weeks | | | | | | | |
| t° C Sub. Cce | | Culture chamber 23° C | | Stove 15° C | | Total | |
| Type of roots | | N | E | N | E | N | E |
| Control | | 1/6 | | 1/6 | | 2/12 | |
| Growth substance | Concentration in μg/l | | | | | | |
| A | 10 | 3/5 | 7/7 | | | 7/12 | 5/12 |
| B | 10 | 5/5 | 4/7 | | | 4/12 | 5/12 |
| A | 20 | 1/6 | 0/6 | | | 1/12 | |
| B | 20 | 5/6 | | 5/6 | | 10/12 | |
| A | 30 | 2/6 | | 6/6 | | 8/12 | |

Table VI-continued

| Number of rooted plants : number of tested plants | | | | | | | |
|---|---|---|---|---|---|---|---|
| Observation at 3 weeks | | | | | | | |
| t° C Sub. Cce | | Culture chamber 23° C | | Stove 15° C | | Total | |
| Type of roots | | N | E | N | E | N | E |
| B | 30 | 5/6 | | 5/7 | | 10/13 | |
| A | 40 | 2/6 | 1/6 | 3/6 | | 5/12 | 1/12 |
| B | 40 | 1/6 | 3/6 | 3/6 | | 4/12 | 3/12 |
| A | 50 | | 4/6 | | 3/6 | | 7/12 |
| B | 50 | 3/6 | | 3/6 | | 6/12 | |
| A | 60 | 2/6 | 2/6 | 0/6 | | 2/12 | 2/12 |
| B | 60 | 2/5 | 1/5 | 3/6 | | 5/11 | 1/11 |

N = normal roots
E = thick roots
A = NAA
B = IBA

The pots were first placed in a minigreenhouse with an 18 hour day length, in about one week they were changed from the saturated atmosphere of the greenhouse to the exterior relative humidity by progressively raising the cover of the greenhouse.

As soon as the plants were strong enough, chromosome numbering were made after fixation and staining by a conventional process known to one skilled in the art. Each "Po" plant revealed a normal number of chromosomes $2n = 18$.

It was observed that the growth of "Po" plants under greenhouse or laboratory conditions was more rapid than that of controls cultured simultaneously. In every case, the "heart" either did not form, or was very small and, with too high a temperature, plants shot up almost immediately. The flower scape developed. The size and total height of the plant were smaller than those of subjects grown normally out of doors.

Thus, on "Po" plants of the variety "Val d'Orge", three modes of development were observed, connected with a more or less long, cool period, in relation to the different seasons, said modes of development observed are given below:

1 Morphogenesis comparable to that of the control

Flowering was induced after a heart had started to form. Selfing, protected by a bag, gave a good crop of about 200 ripe seeds.

2. Plants induced to flower at the time of rhizogenesis

In spite of the small leaves, the flower scape grew and the plant gained in vigour as it grew. Flowering was less significant than with controls and gave a considerable number of fertile seeds as well as some sterile seeds.

3. Plants induced to flower very early, as above, but the vigour of which remained weak Here, the small number of inflorescences was accompanied by practically total sterility of the flower heads, the seeds remaining immature or germinating in the flower heads before the seedbearers had dried.

Seeds obtained from "Po" plants were collected after the seed bearers had dried. The results observed are given in table VII below.

TABLE VII

| "Po", n° of plant | Number of flower heads | Seed collection Number of seeds fertile | sterile | total | Fertile seeds Mean number per inflorescence | rate |
|---|---|---|---|---|---|---|
| 25 | 12 | 59 | 65 / 5 gm | 129 | 4.91 | 0.45 |
| 27 | 13 | 48 | 152 | 200 | 3.69 | 0.24 |
| 24 | 18 | 57 | 157 | 214 | 8.72 | 0.36 |
| 26 | 20 | 94 | 112 / 27gm | 233 | 4.70 | 0.40 |
| 28 | 29 | 177 | 14 / 19 gm | 210 | 9.31 | 0.84 |
| 4 | 40 | 118 | 198 | 316 | 2.95 | 0.37 |
| 9 + 11 | 46 | 214 | 441 | 655 | 4.60 | 0.32 |
| 22 | 46 | 24 | 421 | 445 | 0.52 | 0.053 |
| 19 | 152 | 6 | 890 | 896 | 0.03 | 0.006 |
| t2 | 10 | 262 | — | — | 6.55 | No. 1.00 |
| t4 | 11 | 355 | — | — | 8.65 | No. 1.00 | gm : germinated in the flower head "9" and "11" correspond to "early" and "late" seed collection from a same plant.

For this sample of subjects, the regenerated plants are significantly less fertile than the controls. The variation in the number of flower heads on the various plants cultured under similar conditions should, moreover, be noted. The sum of these results shows the presence of a different response to environment for both the regenerated "Po" plants and controls.

In another connection, the more or less significant degree of sterility due either to a lack of vigour in the plant or to the necessity of strong light, shows the amount of energy required at this stage to obtain flowering and seed ripening.

The seeds obtained from each "Po" regenerated plant represent the "$P_1$" generation of plants: selfing of "$P_1$" subjects gave generation "$P_2$". Generations "$P_1$" to "$P_4$" were studied, and the observations were treated statistically by the method described by P. DAGNELIE (Statistical theory and methods (2 vol.) Presses Agronomiques de Gembloux. Ed. J. Duculot — 1970), notably by variance analysis with two criteria of classification with replication, crossed model and sample of the same effective, by the SNEDECOR test mentioned by DAGNELIE and by the "new range test" method of DUNCAN previously mentioned.

In the "$P_1$" generation it was observed that a family of plants had small hearts compared with controls; the leaves were arranged in a rosette and were matt, with a velvety appearance and not very denticulated; they were neither crinkled nor blistered, so the whole plant had a "flattened" appearance (a).

In the "$P_2$" generation again, homogeneous variant progeny were observed in comparison with the control.

In addition, the appearance of families of a particular colour, and which do not segregate, was observed in the entire population of plants analyzed. Notably, plants with very pale central leaves and dark green veins (c) were observed, and others of a homogeneous paler, golden colour than the controls which are called "blond" plants (b).

Differences were also observed between controls and "$P_1$" plants in as far as concerns the number of leaves in the heart, weight of green matter, number of leaves of axillary buds developed, the number of axillary buds developed, the length and width of the broadest leaf.

The particularities observed for plants (a), (b), (c) of generation "$P_2$" showed the same characteristics in generation "$P_3$" obtained by selfing a randomly chosen representative in each family.

The "$P_3$" families noted a, b, c, as well as the control t with very distinct phenotypes were selected to study the transmission of their character in crossing by the hybridization technique.

Diallel analysis showed that parent "a" possessed the character "flattened leaf" and that it was preferentially transmitted by the seed-parent. Various levels of expression of said character were observed as a function of the parent chosen; it is as thought the various grains of pollen "accept" the cytoplasm of parent "a" more or less readily.

Analysis of the leaf surface, showed that each parent, even when crossed which an isogenic genotype, transmits with crossing a "vigour" both through the pollen plant and the seed-plant, whatever the pairing.

Detailed analysis showed, however, that the intensity of this very particular "vigour" effect is indeed specific to pairing and the direction of crossing. It should be emphasized that the essential and advantageous characteristic of the invention is that more vigorous plants are obtained by crossing on a homozygote plant.

EXAMPLE 7

1. In vitro tissue culture

In this example, tissues obtained from the germination of seeds from a single seed-plant of wheat, variety "Cesar," were cultured in vitro.

The culture medium had the following composition:
A. Basic medium
MILLER microelements and macroelements
FUJII vitamins ($x$ 1)
Glycine $2.10^{-6}$ kg/l
Fe EDTA $10^{-4}$ M
Agar     1 %
Saccharose     12%
B. Growth substance
2.4 D     $2 . 10^{-6}$ kg/l Using this medium, cellular proliferation was obtained and about one month later, the calluses were sufficiently large to be sub-cultured

2. Morphogenesis of calluses

The calluses previously obtained were placed on the morphogenic medium consisting of the above basic medium but having a saccharose content of 2 % and with indolacetic acid ($10^{-6}$ kg/l) as growth substance, the 2,4 D being not present.

3. Potting up

After potting up the plants were first maintained under the environmental conditions used in the morphogenic culture phase and then progressively placed under normal conditions (out of doors).

A certain number of potted plants showed characteristics of variants, notably in as far as concerns vigour and yield.

It is obvious that modifications within the possibilities of one skilled in the art may be brought to the process of the invention without thereby departing from its scope.

We claim:

1. A process for obtaining variants of plants having improved characteristics which comprises the following steps of
   1. placing and culturing, on a non-morphogenic synthetic nutrient medium, tissues obtained from the germination of seed from a single homozygous seed-plant, the said culture medium essentially consisting, firstly, of a basic medium formed of mineral salts, vitamins, iron and saccharose, and secondly, of growth substances in an amount sufficient to ensure callus formation,
   2. sub-culturing the so formed calluses on a morphogenic medium consisting of the above basic medium having different levels of saccharose and growth substances until plants of varying characteristics are formed,
   3. selecting each viable plant, and,
   4. selfing it to obtain a strain thereof.
2. A process according to claim 1, wherein the single seed-plant is an agronomic plant selected from wheat, soya, rape, barley and corn.
3. A process according to claim 1, wherein the single seed-plant is a vegetable selected from lettuces, beans, peas.
4. A process according to claim 1, wherein the seeds are germinated under sterile conditions and that culture on the said media is carried out under sterile conditions.
5. A process according to claim 1, wherein germination occurs at a temperature in the range of about 20° to 23° C.
6. A process according to claim 1, wherein germination occurs in darkness or in daylight with about 8 to 12 hours light.
7. A process according to claim 1 wherein the basic medium contains iron in the chelated form.
8. A process according to claim 7, wherein the chelating agent is ethylene-diamine-tetraacetic acid (EDTA).
9. A process according to claim 1, wherein culturing on the said synthetic nutrient medium is carried out at a temperature in the range of about 18° to 23° C with day lengths of 0 to 18 hours.
10. A process according to claim 1, wherein the said nutrient medium further contains a gelling substance such as agar.
11. A process according to claim 10, wherein the pH of said medium is between 5.7 and 6.5.
12. A process according to claim 1, wherein the calluses are maintained under non-morphogenic conditions for a minimum of 2 to 3 successive sub-culturings before sub-culturing on the morphogenic medium.
13. A process according to claim 1, wherein the pH of the morphogenic medium is in the range of 5.7 to 6.5.
14. A process according to claim 1, wherein the single seed-plant is lettuce and in that the mineral salts contained in the said basic medium consist of macroelements and microelements, the macroelements being potassium and ammonium nitrates, magnesium sulphate, calcium chloride and monopotassium phosphate, the microelements being selected from manganese, zinc and copper sulphates, potassium iodide, boric acid, calcium chloride, molybdenum-sodium oxide, aluminium chloride and nickel chloride.
15. A process according to claim 14, wherein the mineral salts are MURASHIGE and SKOOG macroelements and microelements.
16. A process according to claim 14, wherein the mineral salts are MURASHIGE and SKOOG macroelements and HELLER microelements.
17. A process according to claim 14, wherein the iron contained in the basic medium is chelated with ethylenediamine-tetra-acetic acid and in that the amount of chelated iron expressed as iron is about 5.6 mg/l.
18. A process according to claim 14, wherein the growth substances are selected from the group consisting of α-naphthalene-acetic acid and 6-furfuryl-aminopurine and in that the concentration of each growth substance present in the said nutrient medium is less than or equal to about 1 mg/l of the nutrient medium.
19. A process according to claim 14, wherein the said nutrient medium is a liquid medium further containing casein hydrolysate and coconut milk, the pH of the liquid medium being between 5.5 and 6.5.
20. A process according to claim 1, wherein the single seed-plant is lettuce and in that the calluses obtained in step 1) of the process are sub-cultured onto a first morphogenic medium containing a growth substance inducing the formation of plantlets and in that the plantlets formed are then subcultured on a second morphogenic medium containing a growth substance inducing the formation of roots, said latter medium being called rhizogen medium.
21. A process according to claim 20, wherein the said rhizogen medium is formed of the basic medium such as defined in claim 1, saccharose at a rate of about 20 to 35 g, notably 30 g per liter, and a growth substance selected from the group consisting of α-naphthaleneacetic acid and α-indolebutyric acid.
22. A process according to claim 21, wherein the concentration of growth substance in the said medium is less than 0.1 mg/l.
23. A process according to claim 20, wherein the culture on the rhizogen medium is carried out at a temperature in the range of about 5° to 20° C, and notably 15° C for about 7 to 21 days with about 8 hours day length.
24. A process according to claim 1, wherein the single seed-plant is wheat and in that the basic medium consists of MILLER macroelements and microelements, FUJII vitamins, glycine, iron chelated by ethylene-diamine-tetraacetic acid, agar, saccharose, and in that the growth substance is 2,4-dichlorophenoxyacetic acid.

25. A process according to claim 24, wherein the morphogenic medium consists of the basic medium according to claim 24 having a lower saccharose content and in that the growth substances is α-indolacetic acid.

26. A process according to claim 1, wherein the single seed-plant is soya and in that the synthetic nutrient medium consists of a. a basic medium containing

| | | |
|---|---|---|
| GAMBORG macroelements | 100 | ml/l |
| GAMBORG microelements | 1 | ml/l |
| Fe - EDTA | 10 | ml/l |
| MOREL vitamins | 2 | ml/l |
| Saccharose | 20 | g/l |
| Agar | 7 | g/l and | b. Growth substances

| | |
|---|---|
| 2,4 D | $10^{-4}$ kg/l |
| BA | $2.10^{-7}$ kg/l | pH of the said medium being 5.8

27. A process according to claim 1, wherein the single seed-plant is a homozygote progeny $F_1$ of strain of corn hybrids and in that the synthetic nutrient medium consists of:

a. a basic medium containing MILLER microelements and macroelements

| | | |
|---|---|---|
| Saccharose | 30 | g/l |
| Iron EDTA | $5.10^{-5}$ | kg/l |
| FUJII vitamins | 1 | ml/l | and b. growth substances:

| | |
|---|---|
| 2,4 D | $5.10^{-4}$ kg/l |
| IAA | $5.10^{-7}$ kg/l |
| Kinetin | $10^{-7}$ kg/l |

* * * * *